United States Patent [19]

Bentley

[11] Patent Number: 5,235,732
[45] Date of Patent: Aug. 17, 1993

[54] EMBALMING DRAIN TUBE APPARATUS

[76] Inventor: Hal E. Bentley, 500 Fonville St., Tuskegee, Ala. 36083

[21] Appl. No.: 790,828

[22] Filed: Nov. 12, 1991

[51] Int. Cl.$^5$ .............................................. A61G 17/00
[52] U.S. Cl. ....................................... 27/24.1; 27/21.1
[58] Field of Search ................ 27/23.1, 28, 21.1, 24.1, 27/24.2

[56] References Cited

U.S. PATENT DOCUMENTS

| | | | |
|---|---|---|---|
| 707,775 | 8/1902 | Harris | 27/24.1 |
| 943,464 | 12/1909 | Riley | 27/24.2 |
| 1,477,695 | 12/1923 | Dolge et al. | 27/24.1 |
| 1,522,282 | 1/1925 | Beach et al. | 27/23.1 |
| 4,982,481 | 1/1991 | Deutscher | 27/21.1 |

Primary Examiner—Richard E. Chilcot, Jr.
Attorney, Agent, or Firm—Leon Gilden

[57] ABSTRACT

An embalming tube is arranged for use with an embalming table, wherein the embalming tube is mounted into a cadaver drain tube at a forward end of the embalming drain tube, and a rear terminal end of the embalming drain tube including a rigid conduit mounted in selective securement to a gutter drainage tube in fluid communication with the gutter structure of the embalming table. A modification of the invention includes the embalming drain tube formed of an accordion pleated body for securement in a mounting block arranged for positioning within the embalming table to position the drain tube relative to the central table platform of the embalming table.

1 Claim, 4 Drawing Sheets

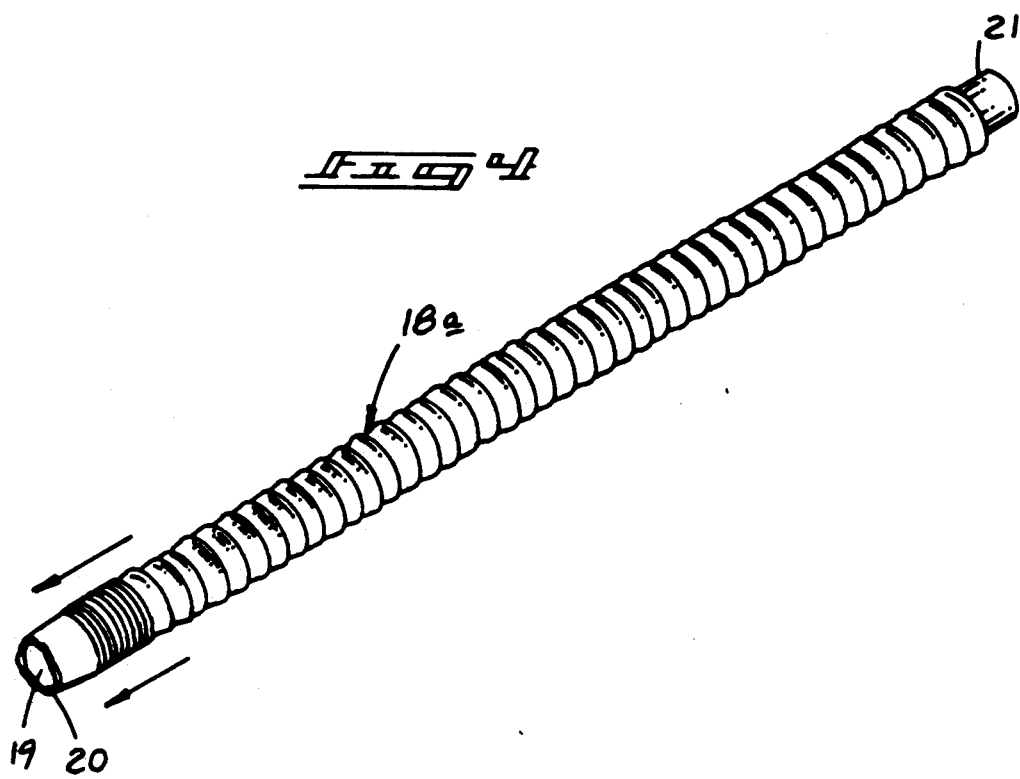
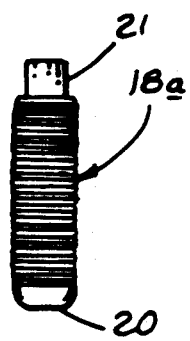
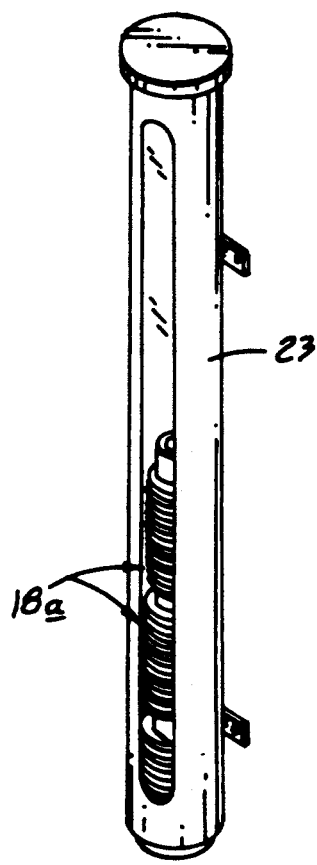

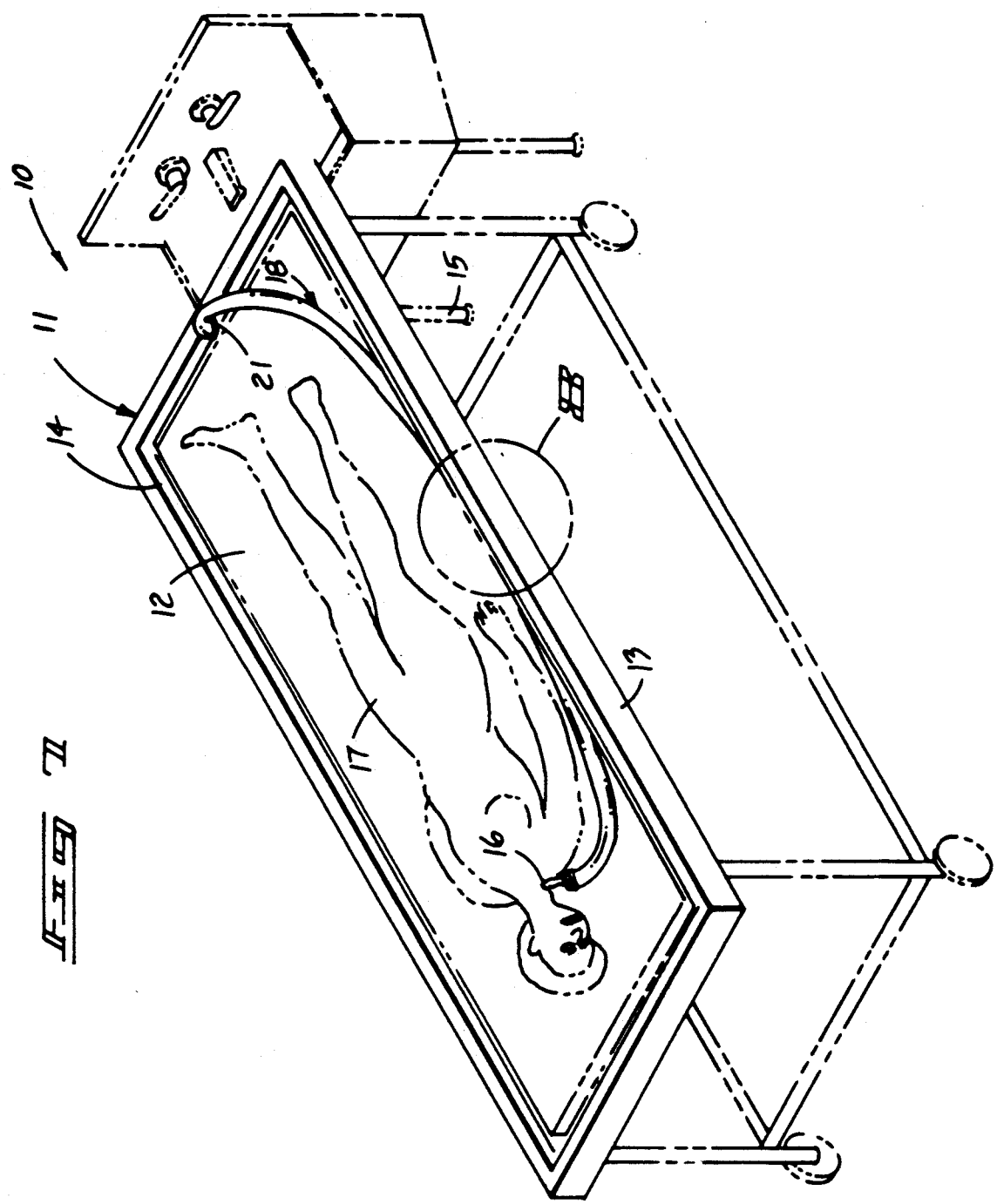
FIG II

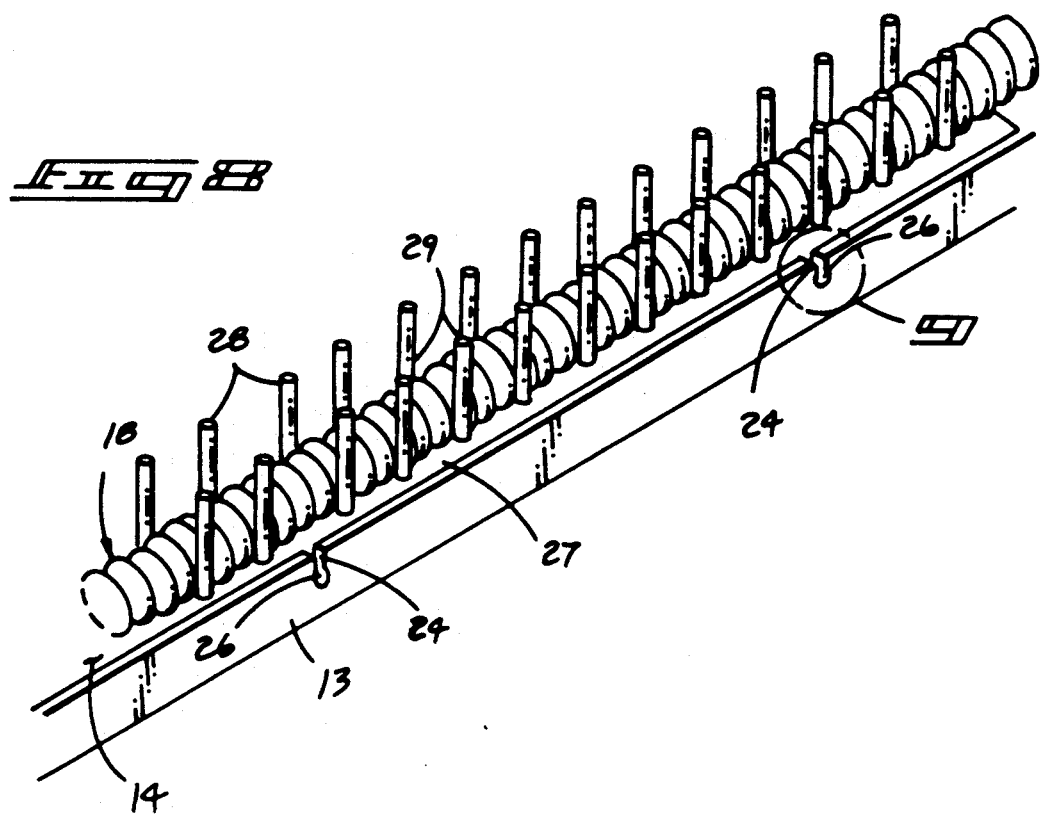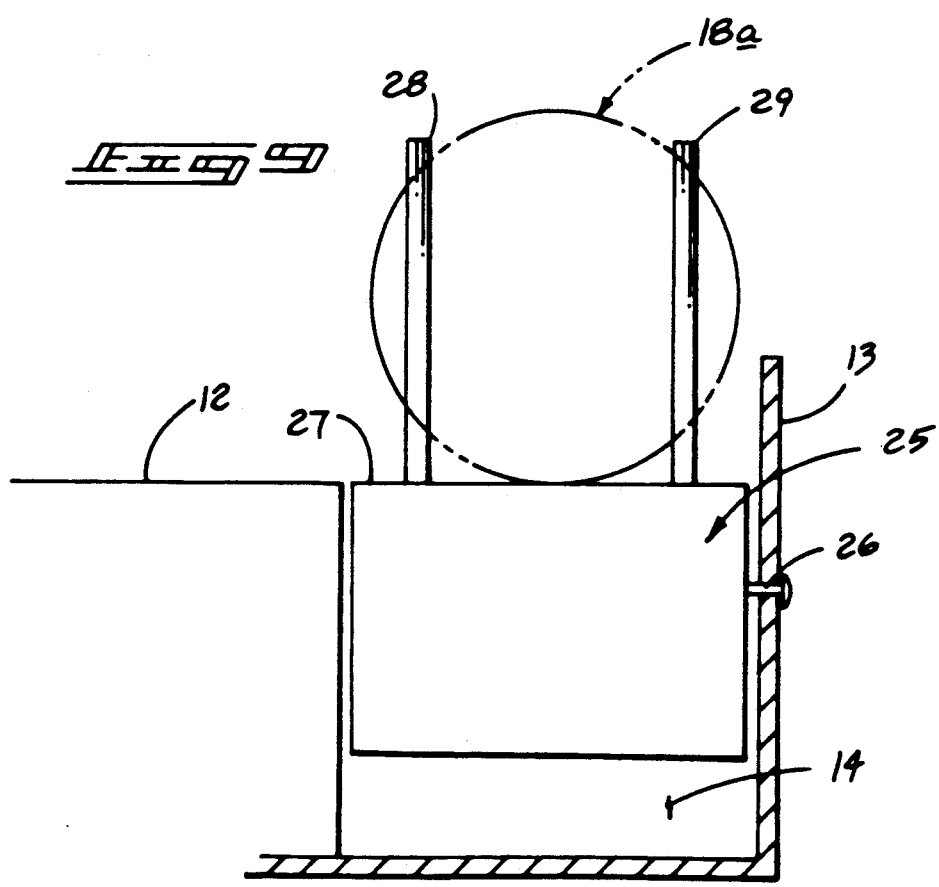

EMBALMING DRAIN TUBE APPARATUS

BACKGROUND OF THE INVENTION

1. Field of the Invention

The field of invention relates to embalming apparatus, and move particularly pertains to a new and improved embalming drain tube apparatus wherein the same is arranged to prevent communication with bodily fluids of a cadaver relative to individuals.

2. Description of the Prior Art

In the drainage or fluid from a cadaver, an embalmer is subject to contact with the drainage of the fluid from an associated cadaver drain tube. Resultant illness in contemporary society creates a hazardous situation in this scenario.

As such, it may be appreciated that there continues to be a need to provide a drain tube in communication with the cadaver drain tube to prevent inadvertent communication of fluid from the cadaver with an operator relative to the embalming table.

SUMMARY OF THE INVENTION

In view of the foregoing disadvantages inherent in the known types of embalming apparatus now present in the prior art, the present invention provides an embalming drain tube apparatus wherein the same is arranged to provide for a closed fluid flow from an associated cadaver into a gutter drain tube of an associated embalming table. As such, the general purpose of the present invention, which will be described subsequently in greater detail, is to provide a new and improved embalming drain tube apparatus which has all the advantages of the prior art embalming apparatus and none of the disadvantages.

To attain this, the present invention provides an embalming tube arranged for use with an embalming table, wherein the embalming tube is mounted into a cadaver drain tube at a forward end of the embalming drain tube, and a rear terminal end of the embalming drain tube including a rigid conduit mounted in selective securement to a gutter drainage tube in fluid communication with the gutter structure of the embalming table. A modification of the invention includes the embalming drain tube formed of an accordion pleated body for securement in a mounting block arranged for positioning within the embalming table to position the drain tube relative to the central table platform of the embalming table.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and the scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved embalming drain tube apparatus which has all the advantages of the prior art embalming apparatus and none of the disadvantages.

It is another object of the present invention to provide a new and improved embalming drain tube apparatus which may be easily and efficiently manufactured and marketed.

It is a further object of the present invention to provide a new and improved embalming drain tube apparatus which is of a durable and reliable construction.

An even further object of the present invention is to provide a new and improved embalming drain tube apparatus which is susceptible of a low cost of manufacture with regard to both materials and labor, and which accordingly is then susceptible of low prices of sale to the consuming public, thereby making such embalming drain tube apparatus economically available to the buying public.

Still yet another object of the present invention is to provide a new and improved embalming drain tube apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an isometric illustration of a modified drain tube structure.

FIG. 5 is an orthographic side view of the drain tube structure in a collapsed configuration.

FIG. 6 is an isometric illustration of a plurality of drain tubes in a dispensing container.

FIG. 7 is an isometric illustration of the apparatus in use.

FIG. 8 is an isometric illustration of section 8 as set forth in FIG. 7.

FIG. 9 is an orthographic cross-sectional view of section 9 as set forth in FIG. 8.

DESCRIPTION OF THE PREFERRED EMBODIMENT

Figure 1:
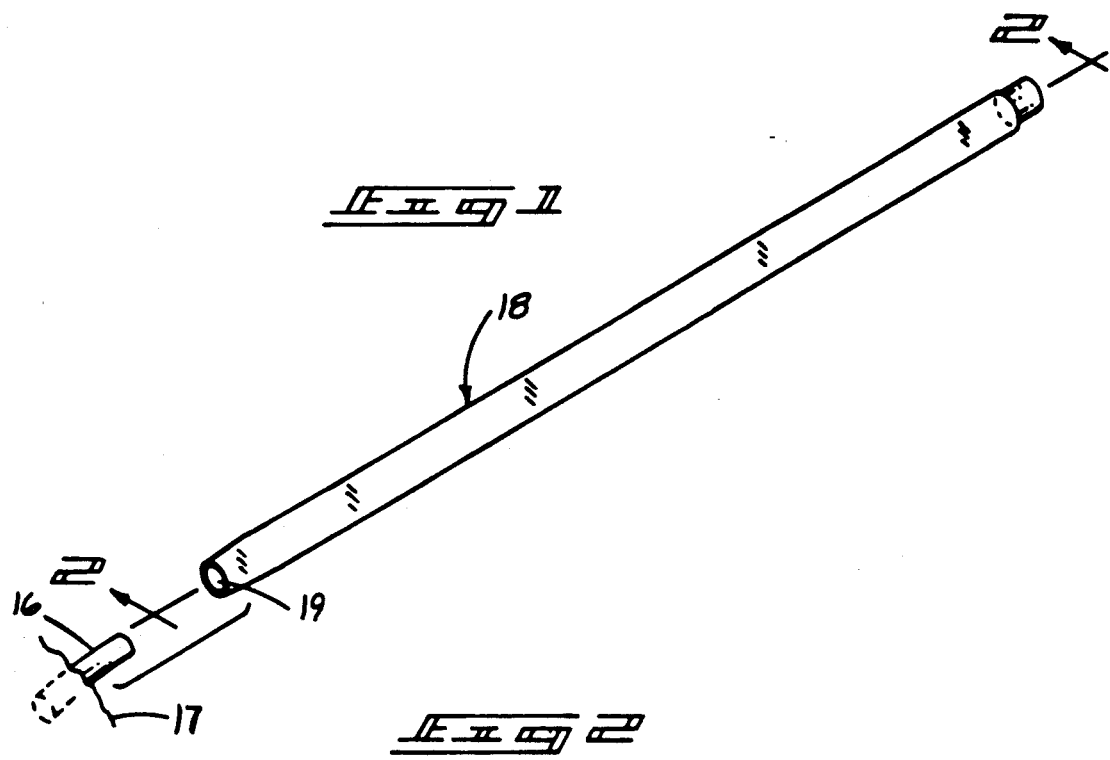
FIG. 1 is an isometric illustration of a drain tube utilized by the invention for association with a cadaver drain tube.
Figure 2:
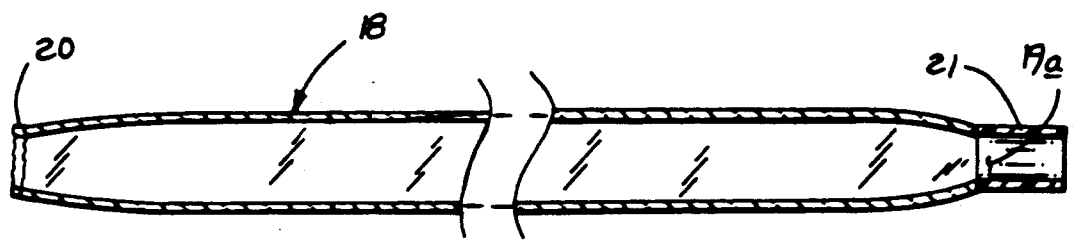
FIG. 2 is an orthographic view, taken along the lines 2—2 of FIG. 1 in the direction indicated by the arrows.

With reference now to the drawings, and in particular to FIGS. 1 to 9 thereof, a new and improved embalming drain tube apparatus embodying the principles and concepts of the present invention and generally designated by the reference numeral 10 will be described.

More specifically, the embalming drain tube apparatus 10 of the instant invention essentially comprises an organization in combination with the embalming table 11, as illustrated in FIG. 7, to include a central table plate 12 positioned medially of a table side wall 13 extending above the table plate 12 and exteriorly thereof defining a continuous perimeter gutter channel 14 coextensively between the table plate 12 and the side wall 13. The gutter channel 14 is defined by a first predetermined width. A gutter drain conduit 15 in fluid communication with the gutter 14 removes fluid therefrom into an associated holding tank and the like (not shown). A cadaver tube 16 is conventionally positioned within the cadaver 17, wherein the drain tube 18 of the invention is formed of a flexible transparent central body, including a forward entrance end 19 and a rear exit end 19a. An elastomeric band 20 is circumferentially mounted above the entrance end for frictional engagement about the cadaver tube 16 in securement thereto. A rigid drain tube rear conduit 21 is mounted to the exit end 19a for securement within the gutter drain conduit 15 to thereby prevent bodily fluids, particularly blond, from contact with an operator relative to the embalming table 11.

Figure 3:
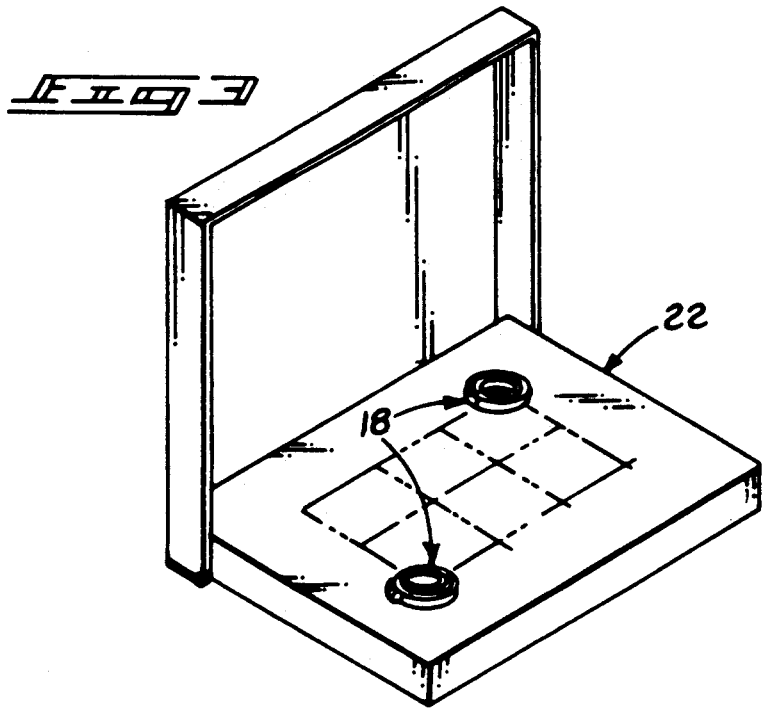
FIG. 3 is an isometric illustration of a support case for mounting the drain tube structure.

As illustrated in FIG. 3, a plurality of such drain tubes 18 are utilized typically once and therefore are provided within a dispensing container 22 containing a plurality of such conduits 18 for use.

FIG. 4 illustrates the use of a modified drain tube 18a, wherein the flexible transparent central body is formed of an accordion pleated construction to permit extension and contraction of the tube for compact storage and ease of manipulation and positioning of the tube in use. A dispensing tube 23 may therefore be utilized for supporting a plurality of such modified drain tubes 18a in a column for sequential dispensing through a bottom of the dispensing tube.

As illustrated, the side wall 13, as illustrated in FIG. 8, includes a plurality of parallel side wall slots 24 orthogonally oriented relative to a top edge of the side wall 13 to mount a support block 25 defined by a second predetermined width less than the first predetermined width to be received within the gutter channel 14 while not obstructing fluid flow into the gutter 14. The support block 25 is formed with a plurality of mounting bosses 26 orthogonally projecting from a side wall of the block 25, wherein each boss is received within a respective side wall slot 24 for positioning the support block 25 in a spaced relationship relative to a floor surface of the gutter channel 14 as illustrated in FIG. 9. The support block top wall 27 includes a plurality of parallel rows of positioning rods defined by a first row of positioning rods 28 and a second row of positioning rods 29 that are arranged in a parallel coextensive relationship relative to one another and spaced apart a predetermined spacing less than the predetermined diameter defined by the body of the modified drain tube 18a to thereby position and receive the accordion pleated body between spaced adjacent pairs of the first and second positioning rods 28 and 29 of the first and second rows to thereby minimize obstruction of the drain tube structure 18a with the central table plate 12 permitting ease of access to the cadaver.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships of the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur in those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An embalming drain tube apparatus, comprising in combination, including, an embalming table,
and
a drain tube, the embalming table including a central table plate, with the central table plate spaced from a table side wall, the table side wall extending above the central table plate and defining a continuous perimeter gutter channel between the table plate and the side wall, with the gutter channel including a gutter drain conduit in communication with the gutter channel directed downwardly therefrom,
and
a cadaver tube arranged for projection within the cadaver,
and
the drain tube including a drain tube forward end, wherein the forward end is arranged for securement to the cadaver tube,
and
a drain tube rear end, wherein the drain tube rear end is arranged for positioning within the gutter drain conduit,
and
the drain tube is formed of a flexible, transparent central body, with an elastomeric band circumferentially formed about the forward end, with the elastomeric band arranged for securement about the cadaver tube, and the drain tube including a rigid drain tube rear conduit secured to the drain tube rear end, wherein the drain tube rear conduit is positioned within the gutter drain conduit,
and the drain tube includes a flexible, transparent accordion pleated central main body defined by a predetermined diameter,
and
the table side wall includes a plurality of parallel side wall slots in communication with and projected downwardly from a top edge of the side wall, and a support block, the support block including a top wall and a side wall, wherein the side wall includes a plurality of mounting bosses, wherein the mounting bosses are spaced apart a predetermined distance and wherein the side wall slots are spaced apart the predetermined distance, wherein the mounting bosses are arranged for sliding reception within the slots, and the support block includes a support block bottom wall, and the gutter channel includes a gutter channel floor, wherein the support block bottom wall is spaced above the gutter channel floor, and the support block includes a first row of first positioning rods and a second rod of second positioning rods, wherein the first row and second row are spaced apart a predetermined spacing less than the predetermined diameter of the drain tube, and wherein the accordion pleated body is projected and removably received between a first row of positioning rods and a second row of positioning rods for containment and positioning of the drain tube relative to the side wall.

* * * * *